(12) United States Patent
Dumm et al.

(10) Patent No.: US 10,952,410 B2
(45) Date of Patent: Mar. 23, 2021

(54) SYSTEM AND METHOD OF ESTIMATING LIVESTOCK WEIGHT

(71) Applicant: DAIRY TECH, INC., Severance, CO (US)

(72) Inventors: Richard H. Dumm, Greeley, CO (US); Timothy Bellis, Fort Collins, CO (US)

(*) Notice: Subject to any disclaimer, the term of this patent is extended or adjusted under 35 U.S.C. 154(b) by 282 days.

(21) Appl. No.: 16/321,659

(22) PCT Filed: Nov. 6, 2018

(86) PCT No.: PCT/US2018/059394
§ 371 (c)(1),
(2) Date: Jan. 29, 2019

(87) PCT Pub. No.: WO2019/090310
PCT Pub. Date: May 9, 2019

(65) Prior Publication Data
US 2021/0045361 A1 Feb. 18, 2021

Related U.S. Application Data

(60) Provisional application No. 62/581,987, filed on Nov. 6, 2017.

(51) Int. Cl.
*A01K 29/00* (2006.01)
*G06T 7/62* (2017.01)
*G06T 17/20* (2006.01)
*G01G 9/00* (2006.01)
*G01G 17/08* (2006.01)
*G06T 7/00* (2017.01)
*G06T 7/70* (2017.01)
(Continued)

(52) U.S. Cl.
CPC .......... *A01K 29/005* (2013.01); *A01K 11/001* (2013.01); *G01G 9/00* (2013.01); *G01G 17/08* (2013.01); *G06K 9/00624* (2013.01); *G06T 7/62* (2017.01); *G06T 7/70* (2017.01); *G06T 7/97* (2017.01); *G06T 17/20* (2013.01); *H04N 5/33* (2013.01); *G06T 2200/08* (2013.01); *G06T 2207/10048* (2013.01)

(58) Field of Classification Search
None
See application file for complete search history.

(56) References Cited

U.S. PATENT DOCUMENTS 6,377,353 B1 * 4/2002 Ellis ................ A01K 11/006
348/135
7,399,220 B2 7/2008 Kriesel et al.
(Continued)

FOREIGN PATENT DOCUMENTS

WO 2017/034776 3/2017

*Primary Examiner* — James A Thompson
(74) *Attorney, Agent, or Firm* — Leyendecker & Lemire, LLC

(57) ABSTRACT

A system and method for estimating livestock weight is described. Embodiments of the system can include a computing device and a three-dimensional tag configured to be secured to an animal. One or more images of an animal, including the three-dimensional tag, can be processed to take various measurements of the animal. A scaling factor for the measurements can be based on the three-dimensional tag. After the measurement are calibrated, a weight of the animal can be estimated based on the calibrated measurements.

15 Claims, 7 Drawing Sheets

(51) Int. Cl.
*H04N 5/33* (2006.01)
*G06K 9/00* (2006.01)
*A01K 11/00* (2006.01)

(56) References Cited

U.S. PATENT DOCUMENTS

| | | | |
|---|---|---|---|
| 8,369,566 B2 | 2/2013 | Sinzinger et al. | |
| 2012/0275659 A1* | 11/2012 | Gomas | G06K 9/48 382/110 |
| 2013/0064432 A1* | 3/2013 | Banhazi | A01K 29/00 382/110 |
| 2013/0314413 A1* | 11/2013 | Coon | G02C 13/005 345/420 |
| 2014/0140582 A1 | 5/2014 | Spicola, Jr. | |
| 2014/0365140 A1* | 12/2014 | Popilka | A61C 19/04 702/19 |
| 2017/0124727 A1 | 5/2017 | Amat Roldan et al. | |
| 2018/0095450 A1* | 4/2018 | Lappas | B22F 3/1055 |
| 2019/0130605 A1* | 5/2019 | Yu | G06T 7/55 |
| 2019/0186981 A1* | 6/2019 | Sugaya | G01B 11/24 |
| 2020/0225076 A1* | 7/2020 | Fournier | G06T 7/62 |

* cited by examiner

SYSTEM AND METHOD OF ESTIMATING LIVESTOCK WEIGHT

CROSS-REFERENCE TO RELATED APPLICATION

This application claims the benefit of U.S. Provisional Application No. 62/581,987, filed Nov. 6, 2017.

BACKGROUND

Obtaining accurate weights for livestock is desirable in order to help determine, for instance, (i) successful mating outcomes, (ii) weight gain on specific food rations, (iii) weight loss due to illness, and (iv) a myriad of other prognostications that are based upon weight and adjustments to weight. The industry is primarily reliant on mechanical means to detect the weight of each individual animal. By utilizing load cells in various sorts of scales, the weight of an animal can be directly or indirectly acquired by a livestock manager. The weighing of each individual animal in a herd on a scale can be both expensive and time consuming requiring the transport of either the scale or each animal to the other. Uncooperative and lively animals can hinder accurate data gathering. Weight tapes that measure girth or other features of a particular animal are also used to estimate its weight. While less expensive, this method can be dangerous, time consuming and is not always accurate.

Other technologies have been used or proposed to estimate the weight of animals within a herd but suffer from one or more shortcomings. Light Detection and Ranging (LiDar), which uses laser imaging to scan an animal and develop a three-dimensional model that can be used to estimate animal weights has been tested. Unfortunately, LiDar devices are expensive and require technical skill to setup and operate.

Photographic systems have been proposed as well wherein an animal is photographed as it passes through the chute. Because the relative distances of the camera to the animal are known and dimensional references can be provided within the field of the photograph, data derived from the photograph can be used to determine relatively accurately an animal's dimensions, which can be used to estimate weight. This process, however, requires funneling livestock through the chute, which can be nearly as time consuming and expensive as the use of a load-cell based scale of which the scale is generally more accurate.

Another proposed system uses a hand-held three-dimensional camera system which includes the capability of calculating distances. The dimensional data from the 3D images can then be used to estimate weights. The system, however, requires a specialized camera and requires an operator to photograph all animals in a herd.

Finally, all of these systems require disturbance of the animal which can create stress and from time to time represents a potential danger to both the animal and the handler. Avoiding stressful contact and unnecessary movement is a key to good animal husbandry.

A non-disturbing system that can calculate a weight of an animal remotely from the animal with high accuracy is needed.

DETAILED DESCRIPTION

Figure 1:
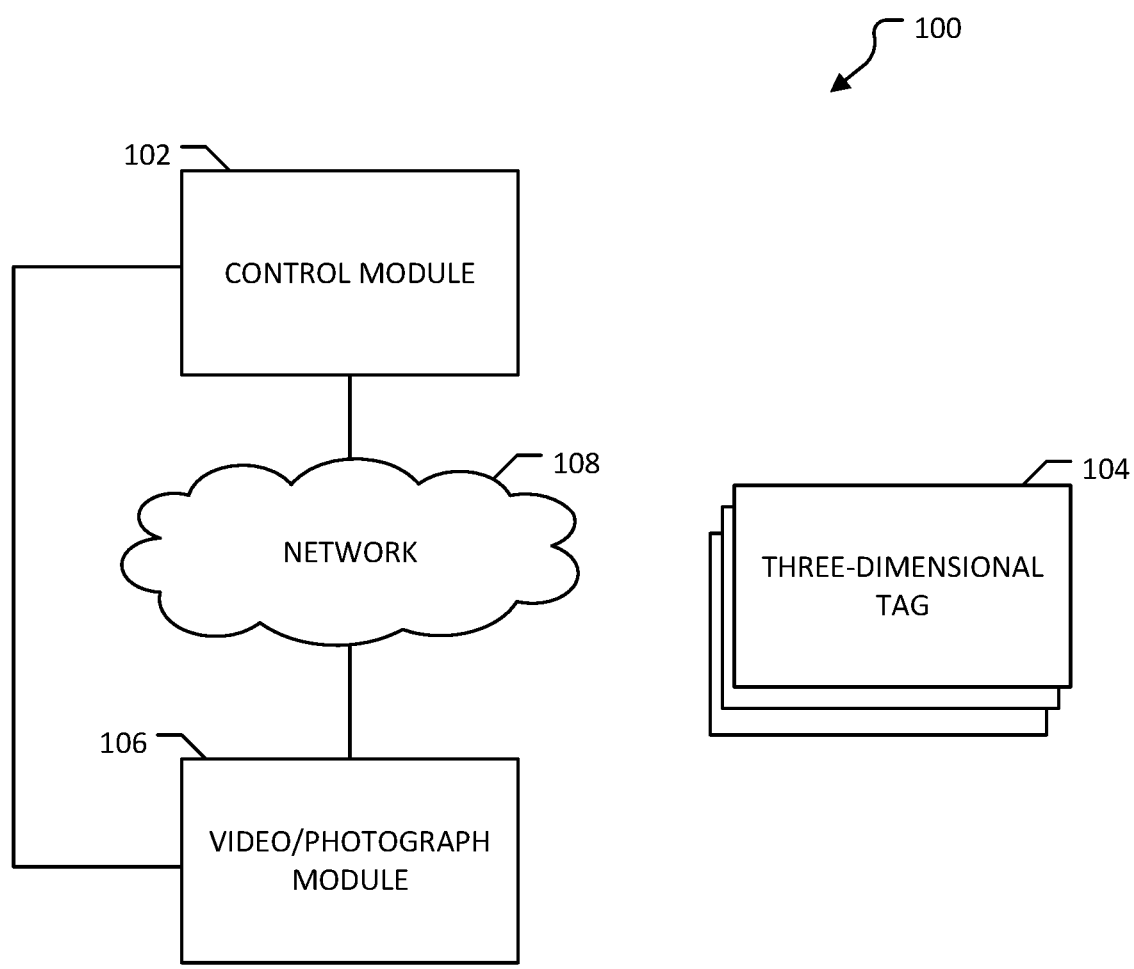
FIG. 1 is a block of a livestock weight estimating system according to one embodiment of the present invention.

Embodiments of the present invention include a system and method of estimating a weight of livestock. Typically, the system can include, but is not limited to, a three-dimensional object and a user device. Images of livestock captured by one or more camera devices can be accessible or obtainable by the user device. In some instances, the user device may be a device that includes a camera and digital storage for storing digital images captured by the camera. The user device can include a program or application configured to calculate an estimated weight of an animal based on measurements taken from one or more images of a livestock animal.

In one embodiment, technology similar to facial recognition software can be implemented to take measurements between landmarks (e.g., shoulder, rear, ear, etc.) on the livestock. The measurements can then be used by the program to calculate an estimated weight of the livestock. Of significant note, the three-dimensional object can be coupled to the livestock to provide a reference of known dimensions for the facial recognition software. In one embodiment, the three-dimensional object can have a ring shape such that an image taken from different angles will allow the facial recognition software to determine a diameter of the ring.

In another embodiment, one or more types of photogrammetry can be implemented to generate a three-dimensional (3D) model of a livestock animal from two or more two-dimensional (2D) images. For instance, stereophotogrammetry can include estimating three-dimensional coordinates of points on an animal by using measurements made in two or more photographic images taken from different positions. Of note, by including the three-dimensional object, images take from different devices or angles can be calibrated to a substantially similar scale.

As can be appreciated, by implementing a ring (or perfectly round ear tag) shaped three-dimensional tag, the diameter of the ring can always be measured regardless of what angle the ring is viewed from. Of note, no matter the skew, the diameter is able to be measured and seen from any point where the ring can be seen. With the diameter of the ring being a known variable, the system can use the measurement as a basis to determine all of the other measurables on the animal. Most other shapes when viewed at various angles will appear and measure shorter or longer. By keeping the design of the tag simple, the tag can serve as a numerical identifier, insecticide tag, etc.

In one embodiment, the three-dimensional object can be a disk. In another embodiment, the three-dimensional object can include at least a circular shape on the object. For instance, a substantially square planar shape may include a circular reference shape ingrained into the object. Alternatively, a circular reference shape may be attached (e.g., a sticker) to the object.

Embodiments of the present invention can include a system and a method of estimating the weight of animals within a group of animals from photographs and videos. Unlike prior art camera-based weight estimating systems, embodiments of the present invention may not rely on photographs taken using specialized cameras or photographs taken from a particular location relative to an animal. The system and method can make use of any photographs taken of a group of animals and even video frames provided the images have suitable resolution. Of note, resolution requirements for photographs can typically be met by most, if not all, modern day phone cameras.

In one embodiment, the weight estimating system can include, but is not limited to, a computer system using specific hardware and/or executing specific software, and one or more three-dimensional tags. Embodiments of the invention can also include methods of using the weight estimating system to estimate the weight of individual animals and/or an entire group of animals. Embodiments of the weight estimating system can further be used in conjunction with still or video cameras. The camera(s) can be used to capture still or moving images of the animals to be analyzed.

The specialized computer system including hardware and software can be similar to computer systems used in facial recognition technology with important and significant differences.

In facial recognition systems, the relative distance or ratios between various features of a face are compared to previously collected information in a database in an attempt to match the face being analyzed to a known person. Because facial recognition systems compare the ratios pertaining to the sizes of different features on the face, the actual size of the features is unimportant and assuming sufficient resolution, they can work whether the subject person is relatively close to the camera, relatively far away, or any distance in between.

In one instance, the weight estimating computer system can analyze video and/or photographic images in a similar fashion as facial recognition systems in determining relative distances between points on a particular animal. The weight estimating computer system may even use this information to identify a particular animal from a database. However, by also measuring the relative distance between two points on the three-dimensional tag, which can be attached to the animal, the weight estimating computer system can determine the actual length between the identified points on the animal. The measurements made by the weight estimating computer system can then be utilized by one or more software algorithms to make mass (or weight) estimations.

The weight estimating computer system can include logic to estimate weight of an animal as well as a database for storing the acquired and calculated data. Some embodiments of the computer system can include modules that format and display the calculated weight information and permit a user to create customized reports.

The three-dimensional tag can be any three-dimensional object adapted to be attached to an animal. The three-dimensional tag can be attached to the animal in a location where at least a side of the tag may be visible from multiple angles or vantage points. For example, for many livestock animals, the tag can be attached to an ear of the animal. Other variations of the tag can be attached at other locations on an animal to ensure the dimensional reference of the tag may be viewable from most, if not many, angles and sides from which an animal may be filmed or photographed. In some embodiments, multiple tags can be placed on an animal. The three-dimensional features of the tag or other device are significant enough to allow viewing from all directions, even in some cases from above via drone. In some variations, the tags can include specific information that identifies the tag as unique. For instance, the tag may include a UPC symbol or QR code that visually identifies the tag and by association, the animal to which the tag is attached. In some embodiments, the tag can contain sensing technologies that are currently used or contemplated in such devices such as radio frequency identification tags (RFID sensing technology) or Bluetooth technology.

In some embodiments, one or more tattoos or branding marks could be used as dimensional references, although it is to be appreciated that marks on the skin or hide of an animal could change dimensionally with weight gain or loss.

To facilitate the estimation of a weight of an animal, video footage and/or photographs of the animal need to be obtained. To accomplish this, any suitable video camera or photographic camera can be utilized. As can be appreciated, digital cameras are often preferred for the ease in transferring the photographic data to the computer system. In one embodiment, the cameras can be dedicated units mounted at strategic locations in a feedlot to monitor and capture images of an animal or a herd thereof. In another embodiment, the camera can be a handheld unit (e.g., a smartphone) that a rancher can use to photograph or record video of a herd in a pasture. The photographic data can be transferred to the computer system in real time, such as through a wired or wireless connection, or the data can be stored in a computer readable media to be downloaded to the computer system at some future point in time.

Described hereinafter is one example method of implanting the previously described weight estimating computer system.

Initially, three-dimensional tags can be attached to each animal a user may want a weight to be estimated for. The tags can be universal or the tags can be unique in configuration. Unique tags can be identified by the specialized computer system to identify the particular animal to which the tag is attached and associated. Each three-dimensional tag can have known dimensions within predetermined tolerances so that the tag data becomes the reference point for the determination of the associated animal's measurements.

Next, photographic images of the tag-bearing animal(s) to be weighed are obtained by any suitable means. In one variation, a rancher can video tape or photograph the animals the user is interested in estimating the weight for. Ideally, each of the animals to be "weighed" can be imaged from two or more vantage points where the three-dimensional tag is also in full view. In another variation, video or photographic cameras are positioned in vantage points where animals, such as those in a herd, regularly pass. As the animals pass they can be photographed. Ideally, the photographic data is digitally rendered although variations are contemplated wherein the photographic data is converted to a digital format in an additional operation such as scanning.

As necessary, the digital photographic data can be transferred to the computer system and converted to a form usable by the system.

In some variations, the software can automatically scan the provided file(s) and identify each different animal shown in the photographic data. Where the photographic data comprises a video, the system may capture several representative still images for each animal from the video for use in calculating an estimated weight. The system may determine the identity of each particular animal by recognizing the unique characteristics of the animal, such as the size and placement of various anatomical characteristics, colorations, hair whirls, brands or marks on the animal. The system may reference previously stored information and associate the images with data concerning known animals and generate new entries for animals not previously stored in the system.

In a less automated variation, an operator of the weight estimating computer system may sort through the photographic data and associate images with particular animals. Where the data comprises video, the operator may identify a representative number of still frames for each animal the operator desires to have a weight estimated for. The information may be stored in folders and/or in database entries for the particular animal.

As can be appreciated the manner in which the photographic data is associated with an animal can vary significantly as indicated by the preceding examples. Ultimately, however, no manner the means of associating photographic data with a particular animal, the process of estimating a weight of an animal can be similar.

The weight estimating computer system can identify relevant points in an image and then calculate the distances between the various points thanks to the presence in the images of at least a side of the three-dimensional tag. By determining the length of an element of the tag in an image, the software can determine the length between various points that were located a similar distance from the camera that originally captured the image. The particular points identified by the software will vary for different animals and the associated weight estimating algorithm.

Once the points have been identified, the computer system can run an algorithm to estimate a weight for the animal based on database information associating weight with certain dimensional parameters. The complexity and accuracy of the algorithm can vary in different embodiments. Some embodiments may utilize a more rudimentary algorithm to obtain a more general estimate of an animal's weight; whereas, other algorithms may utilize more points and distances there between to more accurately estimate weight. Some algorithms may take into account known information about an animal, such as actual scale determined weights and known dimensional parameters at the time of the scale weighing, to make adjustments to the estimated weight and thereby improve accuracy. Advanced variations of the system may include an artificial intelligence component wherein the system analyzes past results either for each individual animal or a collection of animals of the same type to modify the algorithm for greater accuracy.

Once the weight(s) have been estimated, the information can be stored in a database, associated with particular animals, displayed in a chart or graph, or used in any suitable fashion. For instance, the weight estimating computer system can include an analysis package or module with which an operator can look at the changes in a particular animal weight over time or the operator can look at the collective weight changes for a herd of animals. In yet other variations, the system can create a data file for use with popular analysis programs, such as, for instance, Microsoft Excel or Microsoft Access.

In one embodiment, an infrared camera can be implemented to obtain images of the animal(s). For instance, the infrared camera can take images in the 750 nm-1 mm wavelength spectrum. As can be appreciated, this wavelength can penetrate most hair but reflect back off of the skin of an animal. In this manner, the system can potentially eliminate the issue of hair coat impacting a view of the carcass of an animal when estimating weight.

In some embodiments, thermal imaging can be implemented to obtain images of animals. Data can be obtained from the thermal images to be used in calculating an estimated weight of the animal.

In some embodiments, varying anatomical differences combined with color can be used to accurately define a breed of most cattle. Determining a breed of the animal can eliminate some of the variations that a coat of hair may likely impart when estimating a weight of a particular animal. For instance, by knowing the average hair length of different breeds depending on temperature measures, that variable could be eliminated in the weight measurements.

In one embodiment, a method for estimating a weight of an animal can include, but is not limited to, providing a three-dimensional object having known dimensions where the three-dimensional object is a ring with a substantially circular shape, attaching the three-dimensional object to a first animal, obtaining a plurality of images of the first animal with the three-dimensional object attached to the first animal, and processing the plurality of images. The step of processing can include, but is not limited to, identifying the three-dimensional object and the first animal in a first image, measuring a diameter of the three-dimensional object in the first image, calibrating dimensions of the first animal in the first image based on the three-dimensional object in the first image, identifying the three-dimensional object and the first animal in a second image, measuring a diameter of the three-dimensional object in the second image, calibrating dimensions of the first animal in the second image based on the three-dimensional object in the second image, constructing a first 3-D model representing the first animal based on the calibrated dimensions of the first animal in the first image and the second image, and calculating a first estimated weight of the first animal based on the first 3-D model of the first animal.

In another embodiment, the method for estimating a weight of an animal can include, but is not limited to, providing a three-dimensional object having known dimensions where the three-dimensional object being a ring with a substantially circular shape, attaching the three-dimensional object to an animal, obtaining a first image and a second image of the animal with the three-dimensional object attached to the animal where the first image being a side view and the second image being a top view, and processing the images. The step of processing can include, but is not limited to, determining a location of the three-dimensional object in the first image, determining a diameter of the three-dimensional object in the first image, determining a first set of points-of-interest on the animal in the first image, measuring distances between predefined pairs of the first set of points-of-interest in the first image, scaling the measurements based on the known dimensions of the three-dimensional object in the first image, determining a location of the three-dimensional object in the second image, determining a diameter of the three-dimensional object in the second image, determining a second set of points-of-interest on the animal in the second image, measuring distances between predefined pairs of the second set of points-of-interest in the second image, scaling the measurements based on the known dimensions of the three-dimensional object in the second image, and calculating an estimated weight of the animal.

The present invention can be embodied as devices, systems, methods, and/or computer program products. Accordingly, the present invention can be embodied in hardware and/or in software (including firmware, resident software, micro-code, etc.). Furthermore, the present invention can take the form of a computer program product on a computer-usable or computer-readable storage medium having computer-usable or computer-readable program code embodied in the medium for use by or in connection with an instruction execution system. In one embodiment, the present invention can be embodied as non-transitory computer-readable media. In the context of this document, a computer-usable or computer-readable medium can include, but is not limited to, any medium that can contain, store, communicate, propagate, or transport the program for use by or in connection with the instruction execution system, apparatus, or device.

The computer-usable or computer-readable medium can be, but is not limited to, an electronic, magnetic, optical, electromagnetic, infrared, or semiconductor system, apparatus, device, or propagation medium.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiments and are not necessarily intended to be construed as limiting.

The term "software," as used in this specification and the appended claims, refers to programs, procedures, rules, instructions, and any associated documentation pertaining to the operation of a system.

The term "firmware," as used in this specification and the appended claims, refers to computer programs, procedures, rules, instructions, and any associated documentation contained permanently in a hardware device and can also be flashware.

The term "hardware," as used in this specification and the appended claims, refers to the physical, electrical, and mechanical parts of a system.

The terms "computer-usable medium" or "computer-readable medium," as used in this specification and the appended claims, refers to any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium. By way of example, and not limitation, computer readable media may comprise computer storage media and communication media.

The term "signal," as used in this specification and the appended claims, refers to a signal that has one or more of its characteristics set or changed in such a manner as to encode information in the signal. It is to be appreciated that wireless means of sending signals can be implemented including, but not limited to, Bluetooth, Wi-Fi, acoustic, RF, infrared and other wireless means.

An Embodiment of a System for Estimating Livestock Weight

Referring to FIG. 1, a block diagram of an embodiment 100 showing a system for estimating the weight of livestock is shown. The system 100 can be implemented to estimate a weight of livestock based on one or more images of the livestock.

As shown in FIG. 1, the livestock weight estimating system 100 can include, but is not limited to, a control module 102 and a three-dimensional object (or tag) 104. The control module 102 can be implemented to analyze image data and apply one or more algorithms from information generated from the image data to estimate a weight of an animal. The three-dimensional tag 104 can be implemented to provide a scale for the control module 102 to more accurately determine measurements from the image data. The system 100 may further include a video/photograph module 106 and a network 108.

In one embodiment, the control module 102 can represent a computing device or another powerful, dedicated computer system that can support multiple user sessions. In some embodiments, the control module 102 can be any type of computing device including, but not limited to, a personal computer, a game console, a smartphone, a tablet, a netbook computer, or other computing devices. In one embodiment, the control module 102 can be a distributed system wherein control module functions are distributed over several computers connected to a network. The control module 102 can typically include a hardware platform and software components.

As previously mentioned, the three-dimensional tag 104 can be implemented to provide a scale for making measurements on livestock when estimating a weight of the livestock based on images of the livestock. In one embodiment, the three-dimensional tag 104 can have a substantially "ring" shape with a nearly uniform diameter.

The video/photograph module 106 can be implemented to capture images of livestock. In one embodiment, the video/photograph module 106 can be a digital camera. In another embodiment, the video/photograph module 106 can be a digital video camera. In yet another embodiment, the video/photograph module 106 can be a digital camera part of a smart device. For instance, a smart phone camera can be implemented to capture both still images and/or video images. The video/photograph module 106 can be operatively connected to the control module 102. In one embodiment, the video/photograph module 106 can include a network interface 107 that can communicate with the control module 102. The network interface 107 may include hardwired and/or wireless communication protocols to communicate with the control module 102. In some embodiments, the video/photograph module 106 may include removable flash memory for transferring data to the control module 102.

The network 108 can be any type of network, such as a local area network, wide area network, or the Internet. In some cases, the network 108 can include wired or wireless connections and may transmit and receive information using various protocols.

Figure 2:
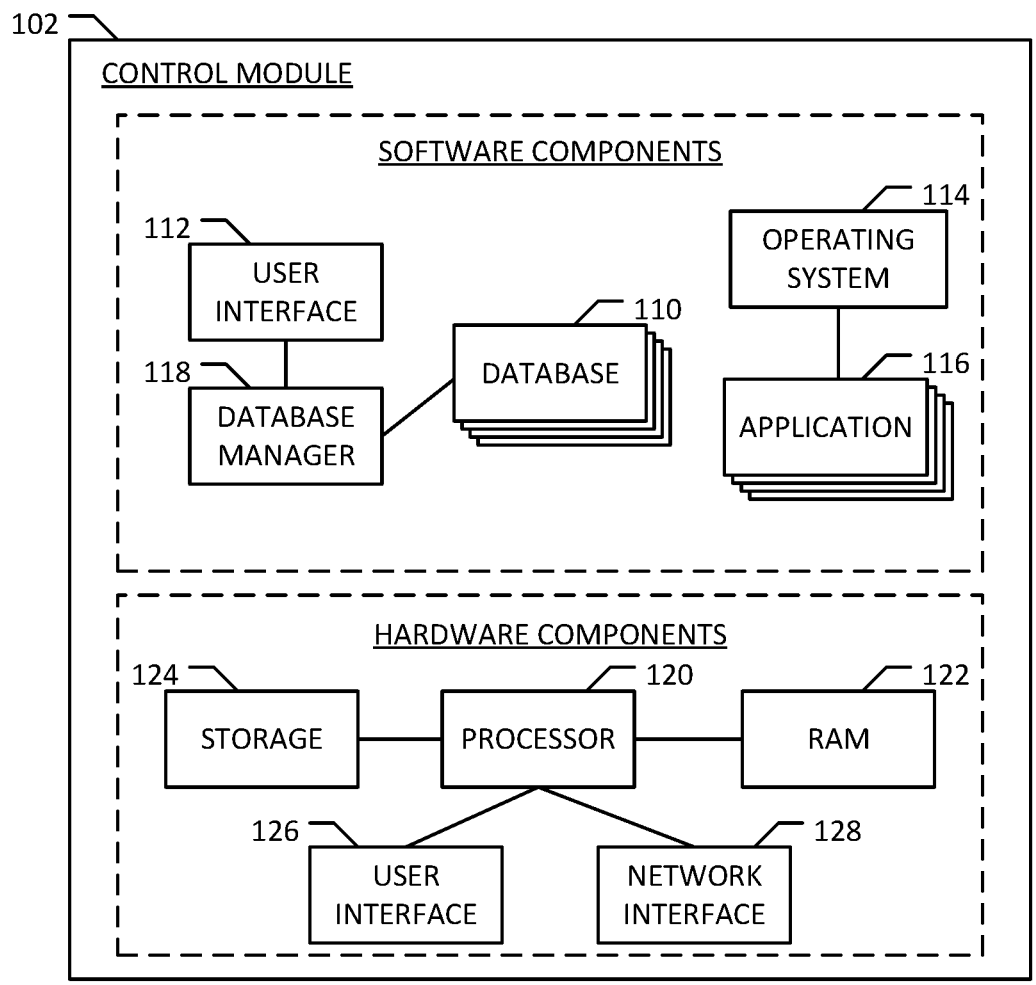
FIG. 2 is a block diagram of a control module of a livestock weight estimating system according to one embodiment of the present invention.

Referring to FIG. 2, a block diagram of the control module 102 is illustrated. The software components of the control module 102 can include one or more databases 110 which can store livestock information and data. The software components can also include an operating system 114 on which various applications 116 can execute. In one embodiment, the control module 102 can include an application dedicated to estimating weight of livestock. For instance, the application can follow a process or method similar to the method described hereinafter. A database manager 118 can be an application that runs queries against the database(s) 110. In one embodiment, the database manager 118 can allow interaction with the database(s) 110 through an HTML user interface on a user device.

The hardware platform of the control module 102 can include, but is not limited to, a processor 120, random-access memory 122, nonvolatile storage 124, a user interface 126, and a network interface 128. The processor 120 can be a single microprocessor, multi-core processor, or a group of processors. The random-access memory 122 can store executable code as well as data that can be immediately accessible to the processor. The nonvolatile storage 124 can store executable code and data in a persistent state. The user interface 126 can include keyboards, monitors, pointing devices, and other user interface components. The network interface 128 can include, but is not limited to, hardwired and wireless interfaces through which the control module 102 can communicate with other devices including, but not limited to, the video/photograph module 106. In some embodiments, the control module 102 can include the video/photograph module 106 and can be implemented to capture images of livestock. In such an embodiment, the control module 102 may be a smart device that can also be implemented to analyze the captured images.

Figure 3:
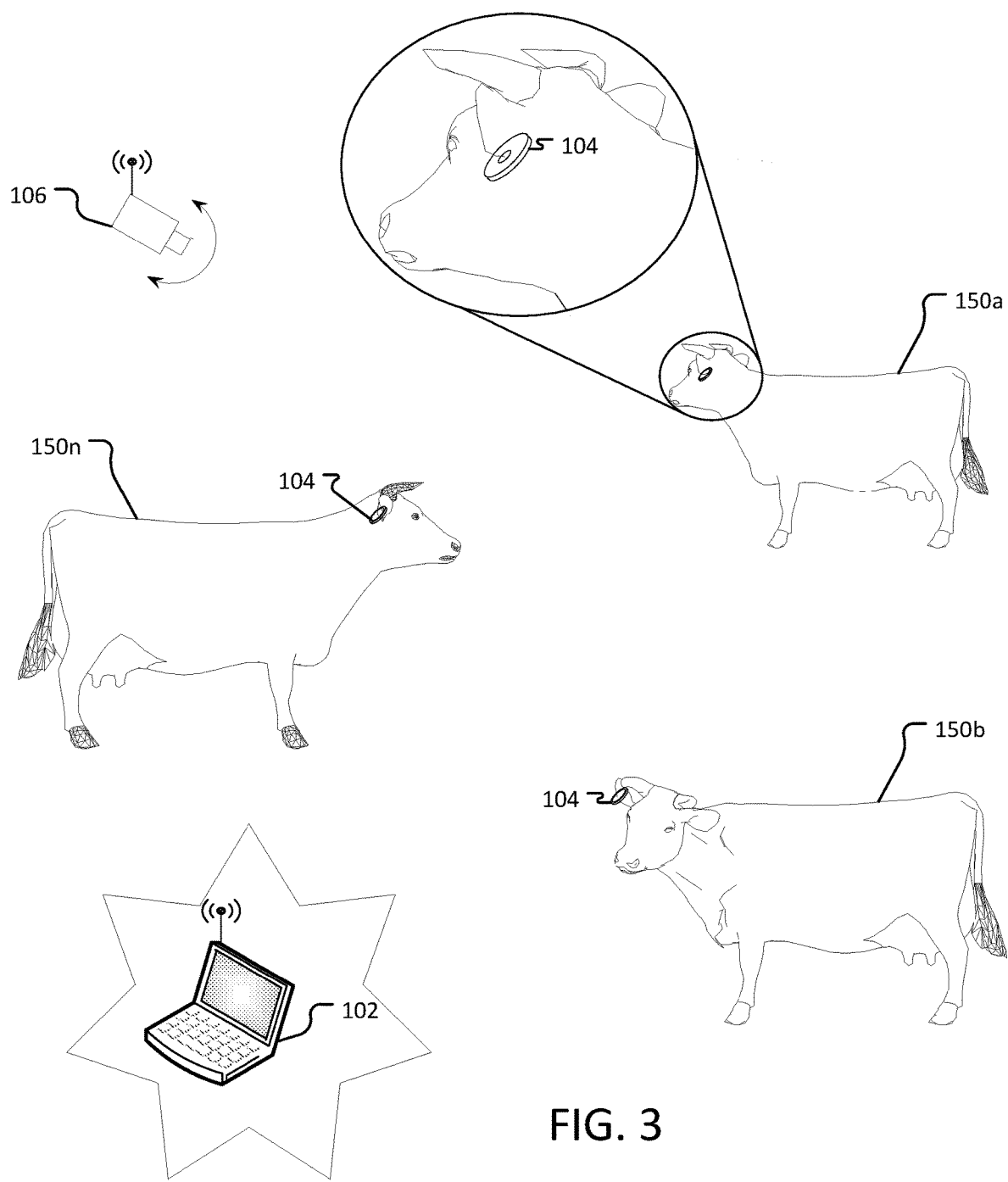
FIG. 3 is a detailed diagram a livestock weight estimating system according to one embodiment of the present invention.

Referring to FIG. 3, a detailed diagram of an example embodiment of the weight estimating system 100 is illustrated. In a typical implementation, the video/photograph module 106 can be located remotely from the control module 102. As previously mentioned, the control module 102 and the video/photograph module 106 may be combined in a single user device. In this example, the video/photograph module 106 will be referred to as the camera.

As shown, the camera 106 may be placed in a pasture where one or more livestock animals, in this instance cattle, are located. The camera 106 can be configured to continuously or intermittently take video and/or photographs of cattle as they pass by the camera 106. For instance, the camera 106 may include a motion detection sensor to activate a video recording function of the camera 106 when cattle pass by the camera 106. In another instance, the camera 106 may continuously record images and stream those images to the control module 102 for storage. A program or application may be implemented to determine when cattle are present in a video frame or image and store those images while discarding or deleting data that does not include images of cattle.

Once images of one or more livestock have been obtained, the control module 102 can analyze the images. In one embodiment, a user may sort each of the images to associate one or more images with each animal the camera 106 captured. Once a set of images has been associated with a particular animal, the application can analyze the set of images to calculate an estimation of a weight of the animal. In another embodiment, the application can be configured to identify a unique identifier on each animal. For example, the three-dimensional tag 104 may include a unique identifier to allow the application to determine which animal is in each image. Of note, other unique identifiers may be used to determine which animals are present in a particular image.

The application can analyze each image taken. Generally, in a first step, the application can determine where the three-dimensional tag 104 is located and determine a diameter of the tag 104. Since the three-dimensional tag 104 can have a uniform diameter that is the substantially the same for each animal, the application can store a distance for the diameter. Once the diameter is determined for a specific image, the application can use the diameter as a scale for the image. After the application has taken various measurements between points of interest, the application can calculate those measurements using the scale based on a diameter of the tag 104.

Figure 4A:
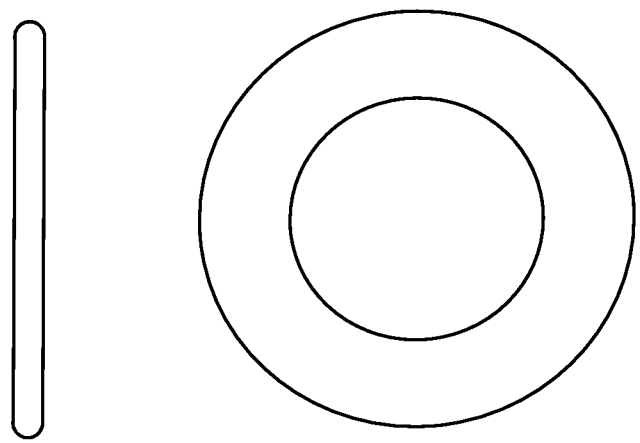
FIG. 4A is a detailed diagram of a three-dimensional object according to one embodiment of the present invention.

Referring to FIG. 4A, one example embodiment of the three-dimensional tag 104 is illustrated. As shown, the tag 104 can be a ring shape with a substantially circular shape. By using a circular ring, the tag 104 can have a uniform diameter such that any measurement of a diameter of the ring would be approximately equal.

Figure 4B:
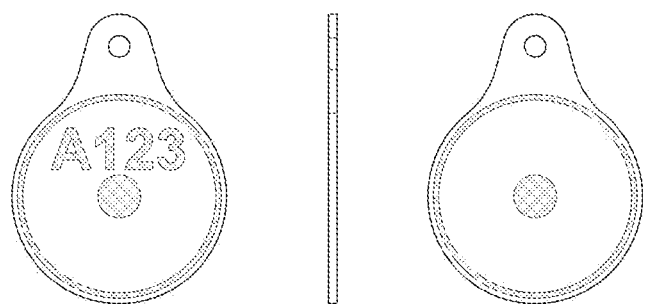
FIG. 4B is a detailed diagram of a three-dimensional object according to one embodiment of the present invention.

Referring to FIG. 4B, another example embodiment of the three-dimensional tag 104 is illustrated. As shown, the tag can have a substantially circular shape with a protrusion extending out to allow the tag to be secured to an ear of an animal. Of note, the tag can include a circular reference marking on each side of the tag. The tag may include one or more alphanumeric characters or other characters to be implemented as a unique identifier for a particular animal. In some embodiments, the circular reference marking can be colored to allow for easy identification. As can be appreciated, other shaped tags may be implemented that include a circular reference pattern.

Figure 5:
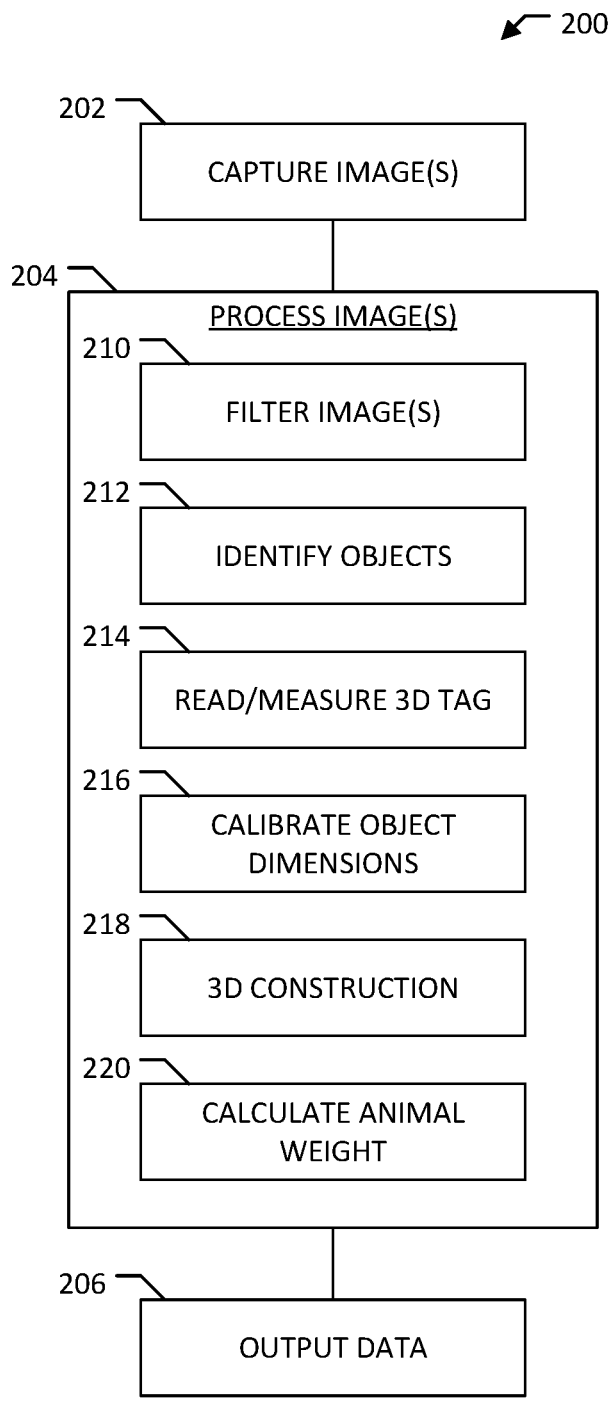
FIG. 5 is a flow chart of a livestock weight estimating process according to one embodiment of the present invention.

Referring to FIG. 5, a first embodiment 200 of a method (or process) for generating an estimated weight of an animal using the livestock weight estimating system 100 is illustrated. It is to be appreciated that one or more steps may be included which are not shown in FIG. 5.

The first method 200 can start with block 202.

In block 202, images of one or more livestock animals can be captured. The means for capturing the images can include a variety of different means and types of devices designed to capture images. Typically, the video/photographic module 106 can be implemented to capture images. As previously mentioned, the video/photographic module 106 may be any one of a plurality of different devices designed to capture images. For instance, a drone including a video and/or still camera can be used to capture images of livestock out to pasture. In another instance, a camera device may be placed on a pole or other type of post in a livestock pasture. In yet another instance, a plurality of camera devices may be implemented to capture images of livestock. As can be appreciated, two or more different types of camera devices may be used together to capture images.

After the images are captured, the images can be processed in block 204. The step of processing images can include one or more of the steps shown in blocks 210-220.

In block 210, the images can be filtered. Typically, a background subtraction process and/or a process for detecting edges, corners, and blobs can be performed. For instance, background modeling or thresholding can be implemented for background subtraction. Processes including, but not limited to, Laplacian of the Gaussian (LoG), Difference of Gaussians (DoG), Sobel operator, Canny edge detector, Smallest univalue segment assimilating nucleus (SUSAN), and Features from accelerated segment test (FAST) can be implemented to detect edges, corners, and blobs.

In block 212, objects in the images can be detected. For instance, the three-dimensional tag 104 attached to an animal can be detected. Further, the animal itself can be detected. One or more of a plurality of processes can be implemented to detect objects in the images. Processes can include, but are not limited to, support vector machines, neural networks, and deep learning to identify objects in the images.

In block 214, after one or more objects in the images have been identified, the three-dimensional tag 104 can be measured and any identifying marks on the tag 104 can be read. Of note, the three-dimensional tag 104 can be measured in each image to create a scaling factor for each image. As can be appreciated, measurements taken in each image can be calibrated to other images since the three-dimensional tag 104 can have predefined measurements. Processes for recognizing text may include, but is not limited to, optical character recognition.

When identifying marks or characters are included on the three-dimensional objects 104, the method 200 may include a step for sorting and compiling images having the same three-dimensional tag 104 together. For instance, where more than one animal is photographed, the method 200 can include a step for sorting the images so that each animal is individually analyzed based on images including said animal.

Once the three-dimensional tag 104 has been measured in the images, object dimensions can be calibrated based on a scaling factor in block 216. Typically, the scaling factor can be determined based on a measurement of the three-dimensional tag 104.

In block 218, each animal detected in the images can be constructed into a three-dimensional (3-D) object (or model). One or more processes can be implemented to generate the 3-D object. Processes can include, but are not limited to, 3D point cloud methodologies and pose estimation methodologies. It is to be appreciated that other means or methodologies of generating three-dimensional models from two-dimensional images are contemplated.

Once a 3-D model of an animal has been constructed, an estimated weight of the animal can be calculated in block 220. One or more processes can be implemented to calculate an estimated weight of the animal based on the 3-D model. Processes can include, but are not limited to: converting point cloud to voxels using octree and sum results; and converting the point cloud to a surface mesh, calculating a volumetric mesh based on the surface mesh, and then summing tetrahedron volumes in the volumetric mesh. In some embodiments, a size and weight database may be implemented to compare the 3-D model of the animal to calculate the weight.

In block 206, data related to the estimated weight of the animal from the processed images can be outputted to one or more devices.

In some embodiments, data related to the steps performed in the method 200 can be stored for historical reference. For instance, the images, a timestamp for each image, any errors in the processing of the images, detection information (e.g., masked images and identified objects), animal identity, calculated animal weight, and feed can be stored by in a database. In one instance, the data can be stored in the database 110 of the control module 102. In another instance, the data can be stored in a remotely located server and/or database.

In some instances, the processing step 204 can be reimplemented when a new image of an animal is obtained. For instance, a camera device may continuously send images to the control module 102 for processing. If processing has already been performed on a plurality of images, the method 200 may reimplement the processing step 204 to include the new images of the animal. As can be appreciated, by including new images, a more accurate 3-D model of the animal may be rendered. Typically, after a new estimated weight has been calculated based on a new image, the previously calculated estimated weight may be deleted.

As can be appreciated, one or more reports may be generated from the data. For instance, a report detailing the weight of animal over time may be generated. A report for the condition of an animal over time may be generated. In another instance, a report showing the correlation of feed and weight gain/loss can be generated to help determine a proper diet for a particular animal or animals. In yet another instance, a report including a comparison between reference data and a particular herd or group of animals can be generated.

Figure 6:
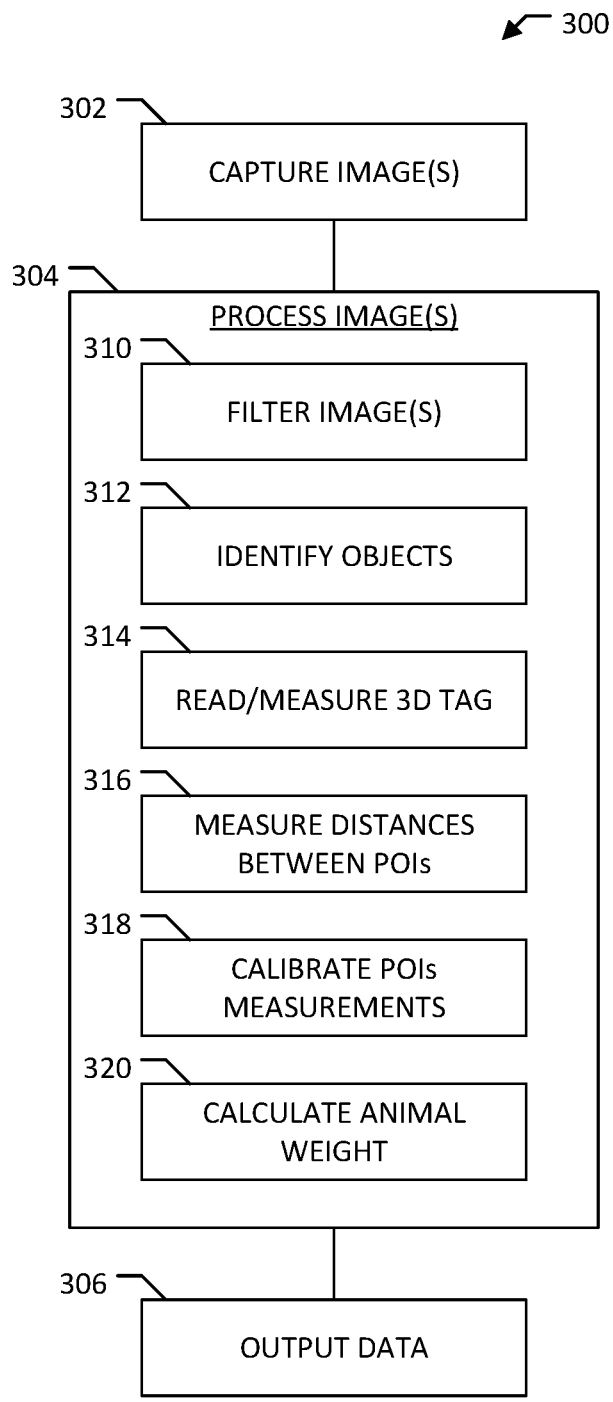
FIG. 6 is a flow chart of another livestock weight estimating process according to one embodiment of the present invention.

Referring to FIG. 6, a second embodiment 300 of a method (or process) for generating an estimated weight of an animal using the livestock weight estimating system 100 is illustrated. It is to be appreciated that one or more steps may be included which are not shown in FIG. 6.

The second method 300 can start with block 302.

In block 302, images of an animal can be captured similarly to the means for capturing images as described in the aforementioned first method 200. Of note, at least a top view of an animal and a side view of the animal can be captured for each animal having a weight estimated for them.

After the images are captured, the images can be processed in block 304. The step of processing images can include one or more of the steps shown in blocks 310-320. Typically, the second method 300 can include blocks 310-314 which include steps and processes substantially similar to the steps and processes included in blocks 210-214 and can be referenced therein for more detail regarding blocks 310-314. In block 310, the images can be filtered. In block 312, objects in the images can be detected. In block 314, after one or more objects in the images have been identified, the three-dimensional tag 104 can be measured and any identifying marks on the tag 104 can be read.

Figure 7:
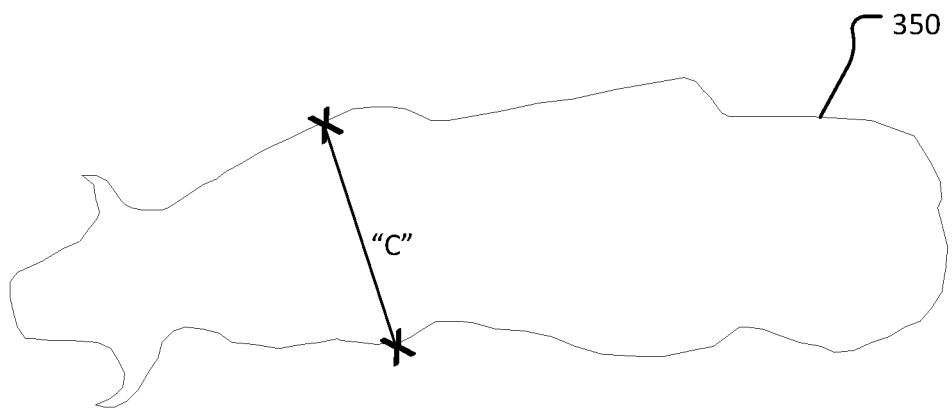
FIG. 7 is a detailed diagram of points-of-interest on livestock according to one embodiment of the present invention.
Figure 7:
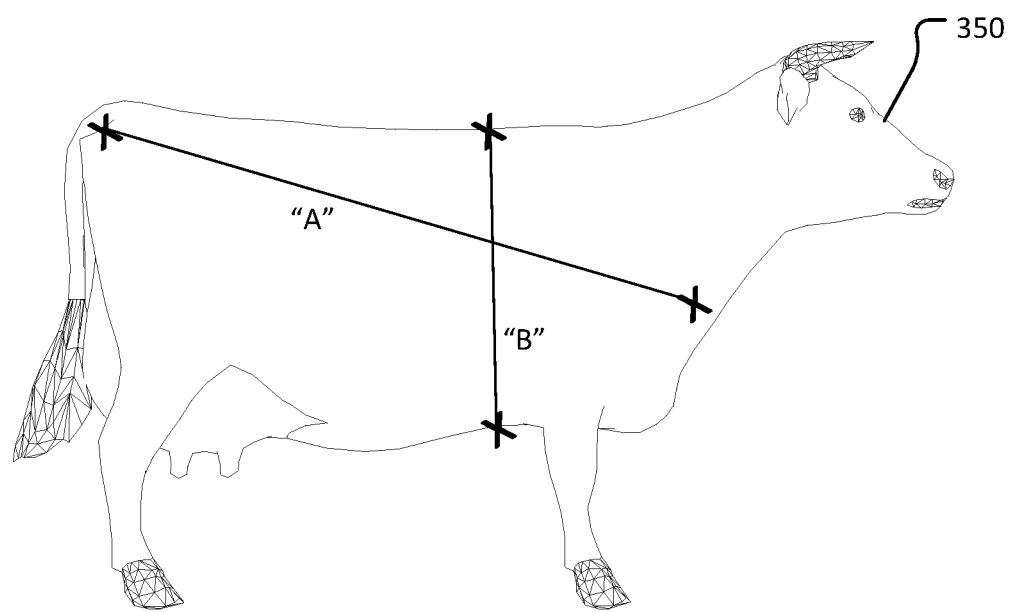

In block 316, a plurality of distances between predefined points-of-interest can be measured. Generally, the points-of-interest can first be determined on the animal in each of the images. Then, measurements between the points-of-interest can be taken. Of note, two or more points-of-interest can be paired together. Points-of-interest can include a plurality of different locations on a body of a livestock animal. Example points-of-interest are shown in FIG. 7 as denoted by an "x" on the cattle. Of note, when estimating a weight of cattle, a side view and a top view of the animal can typically be used. Although cattle are generally shown in the figures, it is to be appreciated that the same techniques can be applied to other types of livestock.

In block 318, the measurements made in the previous step can be calibrated. Similar to the previously described first method 100, a scaling factor can be based on the measurement of the three-dimensional object 104 in the images. As can be appreciated, measurements in each image can be calibrated to increase accuracy of the estimation of weight.

Once each of the image measurements have been calibrated, a weight of the animal can be calculated in block 320. In one instance, a weight can be calculated based on the measurements taken between the points-of-interest. One means for estimating a weight of a cattle is to measure (i) a girth of the cattle in relation to a location of a heart of the cattle, and (ii) a length of a body of the cattle. Then, using the two measurements, a weight of the cattle can be calculated by the equation:

$$G^2 \times L = W$$

In the above equation, "G" represents a measurement of the girth of the cattle, "L" represents the length of the body of the cattle, and "W" represents the cattle weight in pounds. Of note, other parameters may be included to further refine the above equation. For instance, a scaling factor can be included that can be based on the type of cattle. Different breeds of cattle have shorter or thicker hair which can introduce inaccuracies in the above mentioned method of estimating a weight of cattle. As such, the equation may be modified with a scaling factor based on the breed of the cattle to increase accuracy of the estimated weight.

Referring to FIG. 7, a side view and a top view including points-of-interest on an animal 350 for calculating an estimated weight of the animal is illustrated. As shown in the side view, there can be four (4) points-of-interests, denoted by an "X" in the figure, on the animal 350. The two points-of-interest located approximate the front of the animal 350 and the back of the animal 350 can be a measurement "A". The two points-of-interest located approximate the bottom of the animal 350 and the top of the animal 350 can be a measurement "B". Of note, the measurement "A" can be implemented as the length (L) of the animal 350 in the previously mentioned equation. Of note, the measurement "A" may be calibrated with one or more scaling factors to take into account that the body of the animal 350 would be curved and not straight. Therefore, a scaling factor may be implemented to increase an accuracy of the measurement.

As shown in the top view, two points-of-interest denoted by an "X" can be a measurement "C". The measurement "C" and the measurement "B" can be implemented to calculate an approximate girth of the animal 350. As can be appreciated, the animal 350 can have a substantially elliptical cross-section. As such, the measurement "C" can be the minor axis of the ellipse and the measurement "B" can be the major axis. Based on those two measurements, an approximate girth (G) can be calculated by finding a perimeter of the ellipse. The equation for calculating a perimeter of an ellipse is well known and not included herein.

Once a measurement for the girth (G) and the length (L) are calculated, an estimated weight can be calculated based on the above equation.

After the estimated weight has been calculated, the data can be outputted in block 306. The block 306 can be substantially similar to the block 206 in the first method 200.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

We claim:

1. A method for estimating a weight of an animal, the method comprising:
    providing a three-dimensional object having known dimensions;
    attaching the three-dimensional object to a first animal;
    obtaining a plurality of images of the first animal with the three-dimensional object attached to the first animal;
    processing the plurality of images, the step of processing including:
    identifying the three-dimensional object and the first animal in a first image;
    measuring a diameter of the three-dimensional object in the first image;
    calibrating dimensions of the first animal in the first image based on the three-dimensional object in the first image;
    identifying the three-dimensional object and the first animal in a second image;
    measuring a diameter of the three-dimensional object in the second image;
    calibrating dimensions of the first animal in the second image based on the three-dimensional object in the second image;
    constructing a first 3-D model representing the first animal based on the calibrated dimensions of the first animal in the first image and the second image;
    calculating a first estimated weight of the first animal based on the first 3-D model of the first animal.

2. The method of claim 1, wherein the three-dimensional object includes a unique identifier.

3. The method of claim 1, wherein the first 3-D model is a point cloud model.

4. The method of claim 1, wherein the first 3-D model is constructed using pose estimation.

5. The method of claim 1, wherein the three-dimensional object is attached to an ear of the first animal.

6. The method of claim 1, the step of processing further comprising the steps of:
   identifying the three-dimensional object and the first animal in a third image;
   measuring a diameter of the three-dimensional object in the third image;
   calibrating dimensions of the first animal in the third image based on the three-dimensional object in the third image;
   constructing a second 3-D model representing the first animal based on the calibrated dimensions of the first animal in the first image, the second image, and the third image; and
   calculating a second estimated weight of the first animal based on the second 3-D model of the first animal.

7. The method of claim 6, the step of processing further comprising the steps of:
   identifying the three-dimensional object and the first animal in a fourth image;
   measuring a diameter of the three-dimensional object in the fourth image;
   calibrating dimensions of the first animal in the fourth image based on the three-dimensional object in the fourth image;
   constructing a third 3-D model representing the first animal based on the calibrated dimensions of the first animal in the first image, the second image, the third image, and the fourth image; and
   calculating a third estimated weight of the first animal based on the third 3-D model of the first animal.

8. The method of claim 7, wherein (i) data related to the first estimated weight is deleted after the second estimated weight is calculated; and (ii) data related to the second estimated weight is deleted after the third estimated weight is calculated.

9. The method of claim 1, further comprising the steps of:
   providing a second three-dimensional object having known dimensions, the second three-dimensional object being a ring with a substantially circular shape;
   attaching the second three-dimensional object to a second animal;
   obtaining a plurality of images of the second animal with the second three-dimensional object attached to the second animal;
   processing the plurality of images, the step of processing including:
      identifying the second three-dimensional object and the second animal in a third image;
      measuring a diameter of the second three-dimensional object in the third image;
      calibrating dimensions of the second animal in the third image based on the second three-dimensional object in the third image;
      identifying the second three-dimensional object and the second animal in a fourth image;
      measuring a diameter of the second three-dimensional object in the fourth image;
      calibrating dimensions of the second animal in the fourth image based on the three-dimensional object in the fourth image;
      constructing a 3-D model representing the second animal based on the calibrated dimensions of the second animal in the third image and the fourth image;
      calculating an estimated weight of the second animal based on the 3-D model of the second animal.

10. The method of claim 1, wherein the three-dimensional object is a ring with a substantially circular shape.

11. The method of claim 1, wherein the three-dimensional object includes at least a marking having a substantially circular shape.

12. A method for estimating a weight of an animal, the method comprising:
   providing a three-dimensional object having known dimensions;
   attaching the three-dimensional object to an animal;
   obtaining a first image and a second image of the animal with the three-dimensional object attached to the animal, the first image being a side view and the second image being a top view;
   processing the images, the step of processing including:
      determining a location of the three-dimensional object in the first image;
      determining a diameter of the three-dimensional object in the first image;
      determining a first set of points-of-interest on the animal in the first image;
      measuring distances between predefined pairs of the first set of points-of-interest in the first image;
      scaling the measurements based on the known dimensions of the three-dimensional object in the first image;
      determining a location of the three-dimensional object in the second image;
      determining a diameter of the three-dimensional object in the second image;
      determining a second set of points-of-interest on the animal in the second image;
      measuring distances between predefined pairs of the second set of points-of-interest in the second image;
      scaling the measurements based on the known dimensions of the three-dimensional object in the second image;
      calculating an estimated weight of the animal.

13. The method of claim 12, wherein the three-dimensional object is a ring with a substantially circular shape.

14. The method of claim 12, wherein the images are captured by a camera device in the infrared spectrum.

15. The method of claim 12, the step of processing further including the steps of:
   determining a breed of the animal; and
   adjusting the estimated weight of the animal based on the breed of the animal.

* * * * *